United States Patent [19]
Wismer et al.

[11] Patent Number: 5,600,038
[45] Date of Patent: Feb. 4, 1997

[54] ADIABATIC HYDROFLUORINATION OF HYDROCHLOROFLUOROCARBONS

[75] Inventors: John A. Wismer, Washington Crossing; Maher Y. Elsheikh, Wayne; Michael S. Bolmer, Collegeville, all of Pa.; Jean P. Schirmann, Paris, France

[73] Assignee: Elf Atochem North America, Inc., Philadelphia, Pa.

[21] Appl. No.: 410,483

[22] Filed: Mar. 24, 1995

Related U.S. Application Data

[63] Continuation-in-part of Ser. No. 346,489, Nov. 29, 1994.
[51] Int. Cl.$^6$ ............................................. C07C 17/08
[52] U.S. Cl. ............................................. 570/166; 570/168
[58] Field of Search ........................................ 570/166, 168

[56] References Cited

U.S. PATENT DOCUMENTS

| | | |
|---|---|---|
| 3,231,519 | 1/1966 | Clark et al. . |
| 3,287,424 | 11/1966 | Pacini et al. . |
| 3,803,241 | 4/1974 | Stolkin et al. . |
| 3,833,676 | 9/1974 | Ukaji et al. . |
| 3,836,479 | 9/1974 | Paucksch et al. . |
| 3,904,701 | 9/1975 | Schultz et al. . |
| 3,965,038 | 6/1976 | Schultz et al. . |
| 4,091,043 | 5/1978 | Ohsaka et al. . |
| 4,147,733 | 4/1979 | Fiske et al. . |
| 4,937,398 | 6/1990 | Tung et al. . |
| 5,008,474 | 4/1991 | Wairaevens et al. . |

FOREIGN PATENT DOCUMENTS

| | | |
|---|---|---|
| 0234002B1 | 1/1991 | European Pat. Off. . |
| 0421830A1 | 4/1991 | European Pat. Off. . |
| 449617 | 10/1991 | European Pat. Off. . |
| 0486333A1 | 5/1992 | European Pat. Off. . |
| 92/19576 | 11/1992 | WIPO . |
| WO9325507 | 12/1993 | WIPO . |

OTHER PUBLICATIONS

Francis H. Walker and Attila E. Pavlath, Dehydrohalogenation of 1,1,1–Trihaloethanes, J. Org. Chem. (30), Mar. 4, 1965, pp. 3284–3285.

McBeth et al., "Aluminium (iii) Chloride–Chlorohydrocarbon Chemistry, Fourier Transform Infra–red Spectroscopic Studies of the Reactions between Solid Aluminium (iii) Chloride and 1,1,1–Trichloroethane or 1,1–Dichloroethene Vapours," J. Chem. Soc., Dalton Trans., 1990, pp. 671–676.

*Primary Examiner*—Alan Siegel
*Attorney, Agent, or Firm*—Ratner & Prestia

[57] ABSTRACT

Process for adiabatically hydrofluorinating hydrochlorocarbons and hydrochlorofluorocarbons in the gaseous phase in the presence of a catalyst that is active at the initial reaction temperature and remains highly selective at the maximum reaction temperature, e.g., a Cr catalyst. The molar ratio of HF to starting compound is at least about 2.5:1. The initial reaction temperature is selected such that the HF in the feed is partially associated but not completely $(HF)_6$. The catalyst may be unsupported or supported.

22 Claims, 3 Drawing Sheets

ADIABATIC HYDROFLUORINATION OF HYDROCHLOROFLUOROCARBONS

CROSS-REFERENCE TO RELATED APPLICATION

This application is a continuation-in-part application of copending application Ser. No. 08/346,489 filed on Nov. 29, 1994 entitled "Process for the Production of 1,1,1-Trifluoroethane".

FIELD OF THE INVENTION

The present invention relates to continuous gas phase hydrofluorination of hydrochlorocarbons and hydrochlorofluorocarbons.

BACKGROUND OF THE INVENTION

Many hydrochlorocarbons and hydrochlorofluorocarbons (HCFC's) can be converted to hydrofluorocarbons (HFC's) or other HCFC's by direct hydrofluorination, liberating the chlorine from the molecule in the form of HCl. These reactions can use any one of a number of different reactor designs, and can take place in a gas or liquid phase. Gas phase reactions usually have higher selectivity and are well suited to continuous flow systems. The advantages of continuous flow reactors over batch systems from a reactor productivity perspective are well known. In the reactor systems involving HFC's, pressurized reactors have the advantage of allowing the distillation train for product and HCl recovery to be run under pressure, whereby the need for refrigeration is reduced.

One such HFC is 1,1,1-trifluoroethane (R143a), which can be synthesized by hydrofluorination of 1-chloro-1,1,-difluoroethane (R142b). This reaction can take place either in the gas phase or liquid phase. It is well suited to a continuous flow reactor system. In a gas phase reactor, a catalyst is typically required. The reaction is considerably exothermic, so that if the reaction is run under isothermal or near isothermal conditions, substantial cooling is required to take away the heat of reaction.

Another hydrofluorination of interest is that of 1,1,1,2-tetrafluorochloroethane (R124) or 2,2-dichloro-1,1,1-trifluoroethane (R123) to pentafluoroethane (R125). In U.S. Pat. No. 5,334,787 there is described a gas phase reaction for such a system which is near isothermal.

In the design of continuous flow reactor systems, the advantages of plug flow over backmixed or stirred systems is well known. The plug flow reactor is kinetically more efficient and therefore permits higher productivity per unit volume. Furthermore, within the subset of plug flow reactors, the adiabatic reactor has obvious economic advantages over a cooled reactor. Since there is no heat removal in an adiabatic reactor, it can utilize a simple design of a pipe having virtually any diameter. By contrast, a cooled reactor is usually designed as a "shell and tube" reactor having cooling medium on the outside of small diameter tubes, which contain the process fluids and the catalyst. In this type of reactor configuration, changing catalyst can be time consuming and costly. Furthermore, slight differences in the way the catalyst is packed from tube to tube can cause varying pressure drops which result in maldistribution of the feeds among the tubes. For an adiabatic reaction system to work, the catalyst must be selective over a broad range of temperatures. For R143a, this appears to be especially true since literature sources indicate the heat of reaction to be as high as 19 kcal/mol.:

| Compound | $\Delta H_f$ kcal/mol | Reference |
|---|---|---|
| HF | −64.8 | 1 |
| R142b | −116.3 | 2 |
| R143a | −178.2 | 1 |
| HCl | −22.1 | 1 |

Reference 1 is: Reid, R. C., Prausnitz, J. M., and Sherwood, *The Properties of Gases and Liquids*, Third Ed. McGraw-Hill, 1977; Reference 2 is: Benson, S. W. et al., "Additivity Rules for the Estimation of Thermochemical Properties," Chem. Review, 69:279 (1969).

Another important consideration for any gas phase hydrofluorination is the effect of hydrogen fluoride (HF) association. Hydrogen fluoride in both the gas and liquid phase is thought to associate with itself to form an oligomer: $(HF)_n$, $n>1$. The equilibrium between monomer and oligomer is a function of temperature and pressure. For a given pressure, disassociation (sometimes called depolymerization) occurs with increasing temperature. Since this disassociation is considerably endothermic, HF has a very high apparent heat capacity. An illustration of the effects of depolymerization is seen in FIG. 1, which is an enthalpy chart for HF. This chart is taken from Yarboff, R. M., Smith, J. C., and Lightcap, E. H., "Thermodynamic Properties of HF", Journal of Chemical Engineering, Vol. 9, No. 2, 179, April, 1964; Enthalpy is a measure of the heat content of a given system. The straight line 101 at the top of the chart represents the ideal gas region. At the bottom of the chart is the saturation curve 102. The vertical distance between the saturation curve and the ideal gas line represents the heat of depolymerization. The tie lines (e.g., 103) connecting the ideal gas line and the saturation curve provide an estimate of HF enthalpy in the region where HF is partially associated. The relative amount of association can be approximated by the location on the tie line connecting the saturation curve to the ideal gas line. The enthalpy changes occurring in hydrogen fluoride are critical to the design of an adiabatic hydrofluorination reactor.

Other hydrofluorination reactions are thought to behave similarly to the R142b hydrofluorination, for example, the reaction of R124 (1,1,1,2-tetrafluoro-2-chloroethane) to R125 (pentafluoroethane). It is an exothermic reaction (estimated to be about −10 kcal/mol). R124 has a similar boiling point to R142b and has a low boiling azeotrope with HF as does R142b. The dew points of HF mixtures would be expected to be very similar for R124 and R142b.

SUMMARY OF THE INVENTION

The present invention provides a process for making HFC's (or other HCFC's) from hydrochlorocarbons, HCFC's, or any mixtures thereof, using continuous, adiabatic, gas phase hydrofluorination such that the heat of disassociation of HF absorbs a significant portion of the heat of hydrofluorination. The reaction is catalyzed using a catalyst that is sufficiently active to initiate the reaction in the presence of partially dissociated HF and capable of maintaining activity and selectivity at elevated temperatures. A typical catalyst for this type of reaction would be a chromium salt, alone or together with a cocatalyst selected from the group consisting of nickel, cobalt, zinc and manganese salts. The catalyst could be supported or unsupported.

The applicable starting compounds for hydrofluorination in this type of adiabatic process are of the type RCl, with R having the general formula $C_wH_xCl_yF_z$, where w is an integer from 1 to 4 and the sum of (x+y+z) is either 2w+1 or 2w−1 (for monounsaturated compounds). The major criterion in judging a reaction's suitability for the process of the invention is the normal boiling point (or dew point if a mixture) of the starting hydrochlorocarbon or HCFC, which must be lower than 60° C. and preferably lower than 50° C. If the boiling point or mixture dew point is higher than this, the HF will be disassociated by the time the feed is vaporized, and its effective heat capacity will be significantly diminished. The hydrofluorination reaction must also be exothermic, with the size of the exotherm being greater than 2 kcal/mol and less than 20 kcal/mol.

In its basic form, the invention provides a method whereby HFC can be made from hydrochlorocarbon and HCFC feeds at very high conversion and selectivity using a very simple and economical reactor design and a very specific range of initial temperatures and HF/HCFC molar feed ratios.

The process of the present invention results in the formation of less than 10 ppm olefin by product.

DETAILED DESCRIPTION OF THE INVENTION

Figure 1:
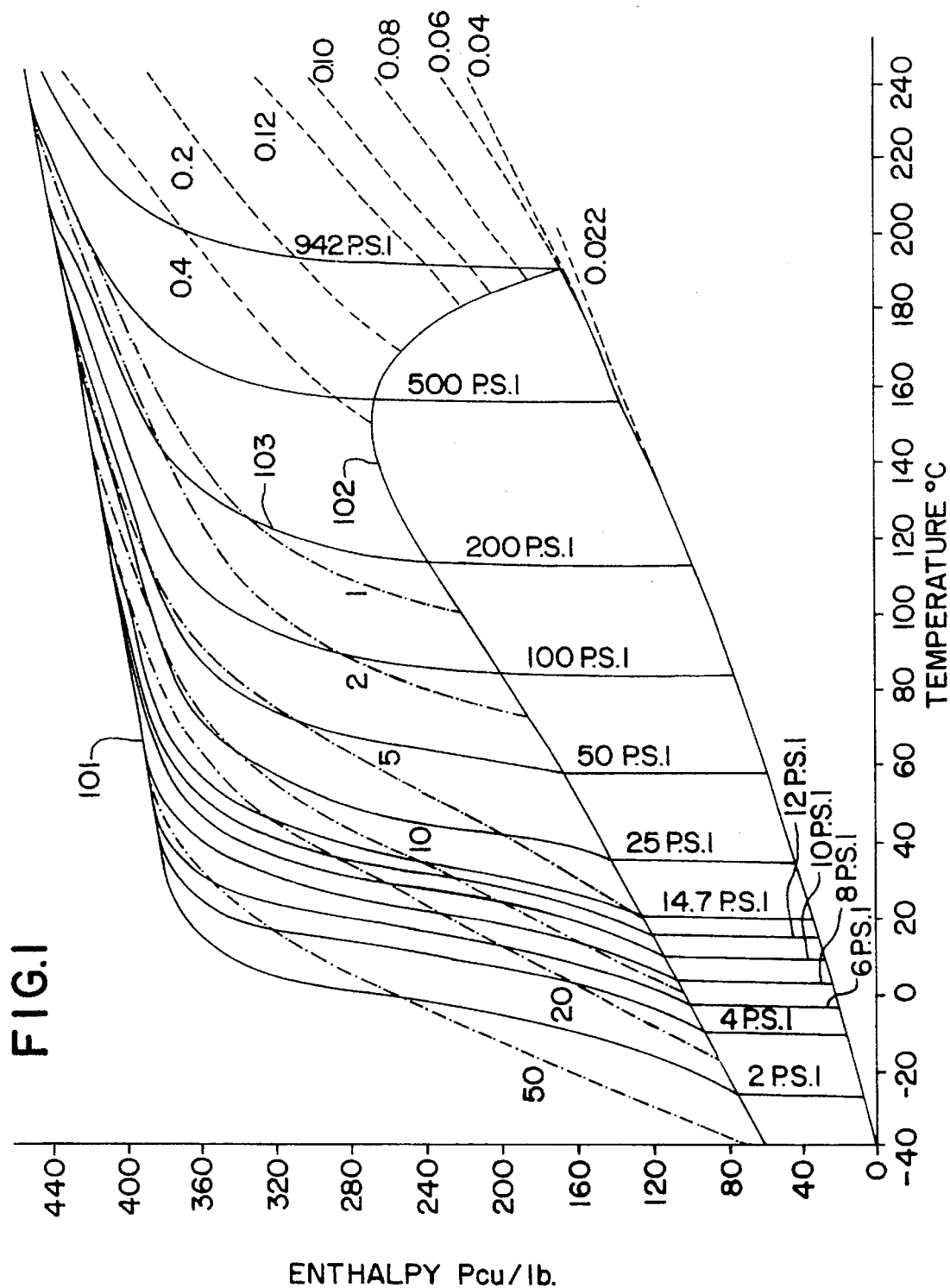
FIG. 1 is an enthalpy-temperature diagram for anhydrous HF.

The process of the invention comprises reacting HF and HCFC or hydrochlorocarbon vapors in a continuous, plug flow adiabatic reactor utilizing a selected catalyst. The HCFC or hydrochlorocarbon reactants are selected from the family of compounds of the type RCl, with R having the general formula $C_wH_xCl_yF_z$, where w is a number from 1 to 4 and the sum of (x+y+z) is either 2w+1 or 2w−1. In the case of pure component feeds, the HCFC (or hydrochlorocarbon) must have a normal boiling point below 60° C. and preferably below 50° C. If the feed is a mixture of HCFC's (and/or hydrochlorocarbons), the mixture dew point must be below 60° C. If the normal boiling point or mixture dew point is too high, the HF is entirely disassociated at the feed composition dew point and the benefits of enhanced HF heat capacity are not realized. Preferred compounds for this technology are those for which w=2, y=0, and (x+y+z)=2w+1.

The focus of the experimental work was on the hydrofluorination of R142b to R143a. However, this technology can be applicable to systems such as the hydrofluorination of R124 to R125.

In the case of R143a, it was surprising to find that the adiabatic design was feasible, since the heat of reaction as measured by the experimental program (about −9.5 kcal/mol) was less than suggested by the literature, and the reaction could be initiated at temperatures where the HF is partially associated. The reactor design disclosed herein makes novel use of HF association to control both the extent and the rate of the adiabatic temperature rise.

At the same time, it was also found that highly associated HF was essentially unreactive in an adiabatic system. Therefore, the permissible temperature window for initiating the adiabatic reaction is narrow. However, depending on pressure, this window may range from 40° C. to 170° C. In one aspect of this invention, that window is defined as a function of feed conditions. Also, to avoid coking, the maximum reactor temperature should not be allowed to exceed 400° C.

The reactor pressure can vary from 1 atmosphere to 500 psig with a preferred range being between 50 and 250 psig.

Unlike most gas phase reactor systems, increasing pressure at constant temperature slows the reaction. This is probably due to the higher pressures causing increased HF association. Surprisingly, the catalyst was selective over a broad range of reaction temperatures, provided that plug flow was maintained. An HF ratio well in excess of stoichiometric was needed to prevent disproportionation of R142b to R141b, 143a, 140a, and subsequent decomposition to olefinic compounds. It is particularly important to avoid olefinic compounds because they are believed to be precursors to coke formation, which, in turn, can deactivate the catalyst. In accordance with this invention, it has been found that the required initial temperatures and HF/R142b molar feed ratios needed to produce R143a at very high selectivity, and very high reactor productivity are, respectively, about 90° C. to about 140° C. and about 2.5:1.

For the hydrofluorination to F143a, the feed can also be a combination of R142b and R141b (1,1-dichloro-1-fluoroethane). Usually, the fluorination of the two chlorine HCFC to the one chlorine HCFC is not very exothermic and can even be endothermic. Therefore, the impact on temperature rise from using a mixed feed is minimal.

The hydrofluorination reaction must also be exothermic, with a net exotherm between 2 and 20 kcal/mol of HF. For an exotherm below 2 kcal/mol, the adiabatic temperature rise is not severe enough to require a heat sink. For exotherms above 20 kcal/mol, the heat sink would not be large enough at practical HF feed rates to have a significant impact. Thus, R124 is thought to have a heat of reaction of about 10 kcal/mol and its normal boiling point is −12° C. (as compared to −9.2° C. for R142b). Like R142b, it also has a low boiling azeotrope with HF.

The adiabatic reaction process requires a catalyst which is sufficiently active at the temperatures where HF is significantly associated (the actual temperature range is a function of reaction pressure) and yet maintains its selectivity at elevated temperatures. A typical catalyst that is suitable for this type of process is a chromium salt, alone or together with a cocatalyst selected from the group consisting of nickel, cobalt, zinc, and manganese salts. The catalyst can be supported or unsupported. Typical supports would be $AlF_3$ or fluorinated alumina. A preferred catalyst is a chromium salt, with a nickel salt cocatalyst on an $AlF_3$ support. The preparation of this catalyst is described in copending U.S. patent application Ser. No. 08/346,489, entitled, "Process For The Production Of 1,1,1-Trifluoroethane," filed on Nov. 29, 1994, the specification of which is incorporated herein by reference.

If the reaction is to run properly, a narrow range of initial temperatures must be employed. This initial temperature is a function of the HF and HCFC/hydrochlorocarbon mol fractions in the feed. It is obvious that the feeds must be at a temperature in excess of the mixture dew point in order to react in the vapor phase. However, in spite of the high activity of the catalyst, it is necessary to heat the feeds considerably above the dew point in order to get a reaction.

Presumably, this is so that the HF is disassociated enough for monomeric HF to react. However, reacting completely disassociated HF at very high initial temperatures can result in very high reactor temperatures (since the moderating effect of the heat of dissociation of HF is absent), which causes non-selectivity. It can also give a very narrow reaction zone with a very high temperature gradient. This narrow temperature zone is undesirable in adiabatic reactors because it can lead to very high temperature transients when the system is disturbed. In most gas phase reaction systems, increasing the pressure at a given temperature will increase the rate of reaction. In the region studied, the apparent rate of reaction can drop with increasing pressure in that a higher initial temperature is needed to achieve the same productivity. This is thought to be caused by increasing HF association into the substantially unreactive oligomeric form with increasing pressure.

One approach to specifying the acceptable range of initial temperatures uses the HF enthalpy chart of FIG. 1. This method can be used for any feed system containing an HCFC (or hydrochlorocarbon) with an appropriate boiling point. Using FIG. 1 as a guide, the enthalpy difference between the feed HF at its calculated ideal gas partial pressure and saturated HF at the same pressure should be at least 35% and not more than 90% of the difference between the saturated HF enthalpy and the ideal gas HF enthalpy. This difference is a measure of the degree of association of the HF. For the case of the F142b reaction to F143a at 110 psig (or 125 psia [psia=14.7+psig]) and a 4/1 molar ratio of HF to F142b feed, this would mean an initial reaction temperature range of 90° C. to 142° C. This range is calculated by first calculating the HF partial pressure (0.8× 125 psia=100 psi); then observing that the enthalpy distance between the ideal gas line and the saturation curve is about 230 Pcu (430–200), or about 414 Btu (1 Pcu=1.8 Btu). At 35% of this enthalpy difference, the temperature is 90° C. at an HF enthalpy of 280 Pcu/lb. At 90% of this difference, the temperature is about 142° C. at an enthalpy of 407 Pcu/lb. For the F142b hydrofluorination, a preferred range was found to be an HF feed enthalpy between 50% and 90% of the ideal gas and saturation curve difference. This would translate to between 100° C. and 142° C. in the above example.

Figure 2:
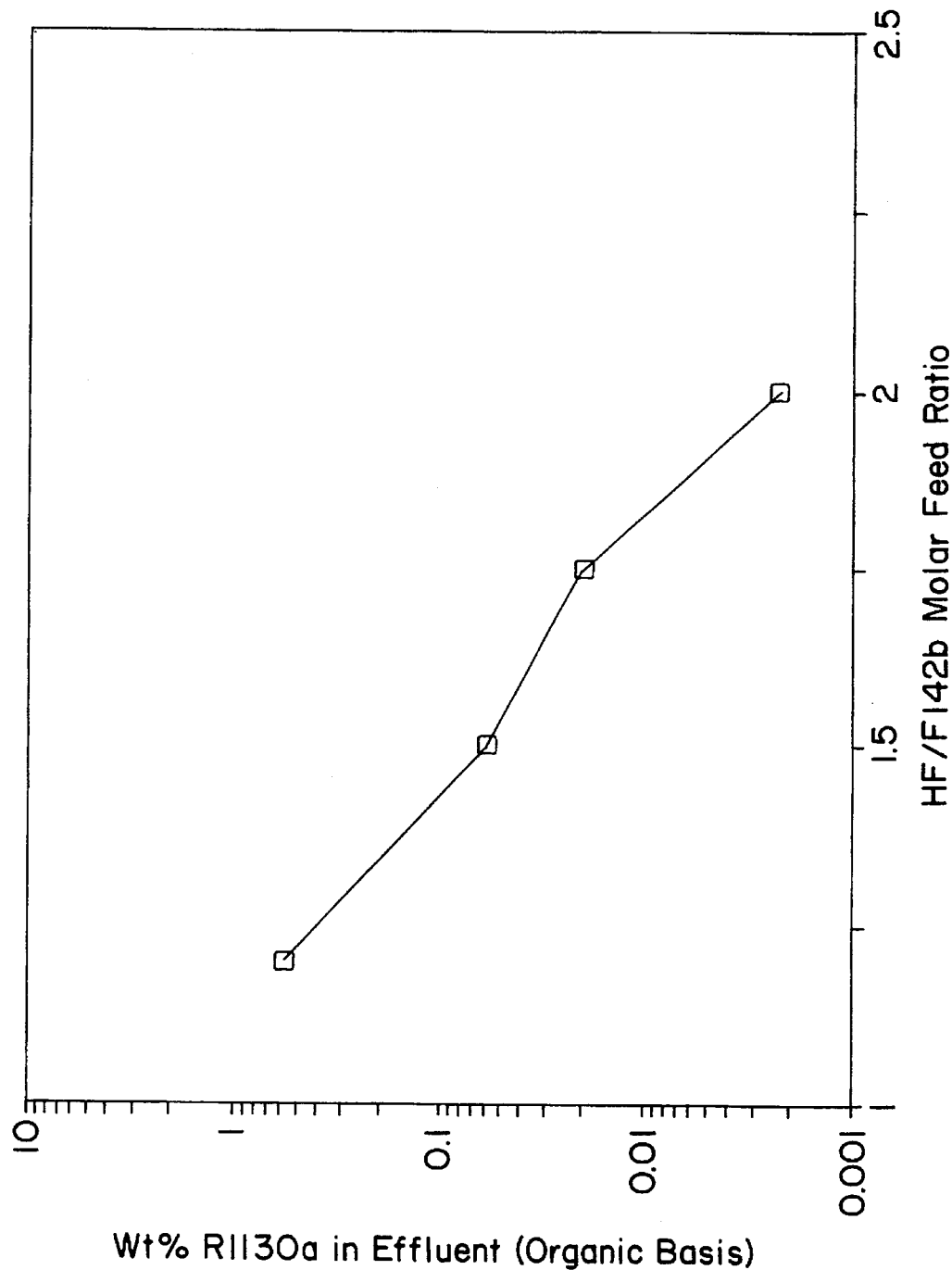
FIG. 2 is a graph showing the percentage of Vinylidene chloride (VDC) formation at different feed ratios of HF/142b when the hydrofluorination is performed adiabatically at a pressure of 130 psig.

Another important parameter is the ratio of HF to HCFC/ hydrochlorocarbon in the feed. Ideally, this would be very close to 1 to minimize downstream separation. However, at low HF ratios, non-selectives are formed. In the case of the R142b hydrofluorination, three different types of olefins can form: vinylidene fluoride (R1132a), vinylidene chlorofluoride (R1131a), and vinylidene chloride (R1130a). These are decomposition products of R142b. Normally, the relative rates of the decomposition reactions are such that the ordering of olefin quantities in the effluent stream is: R1130a>R1131a>R1132a. These unsaturated compounds are undesirable in the final product even in small quantities. Therefore, they must be either chemically converted to saturated compounds or removed by a separation method after passing out of the reactor. These olefins are also precursors to coke formation, which is the major cause of catalyst deactivation. We have found that at HF/R142b mol ratios of 2.5/1 in the feed, virtually no olefins are formed (i.e.<5 ppm). The olefin formation rates increase logarithmically at HF/R142b mol ratios below this, as shown in FIG. 2. Two factors are thought to be important in olefin formation: temperature and HF concentration. The higher the HF/R142b ratio, the lower the maximum bed temperature. There is no upper limit on HF/R142b ratio, although ratios above 10/1 would be economically impractical, both with respect to reactor productivity and separation requirements.

As indicated above, the R143a synthesis technology could also be applied to the use of mixtures of R141b and R142b as feedstocks. This is because the R141b to R142b reaction has a very mild exotherm (about 1 kcal/mol), which makes the net exotherm to R143a about 5 kcal/mol of HF.

Figure 3:
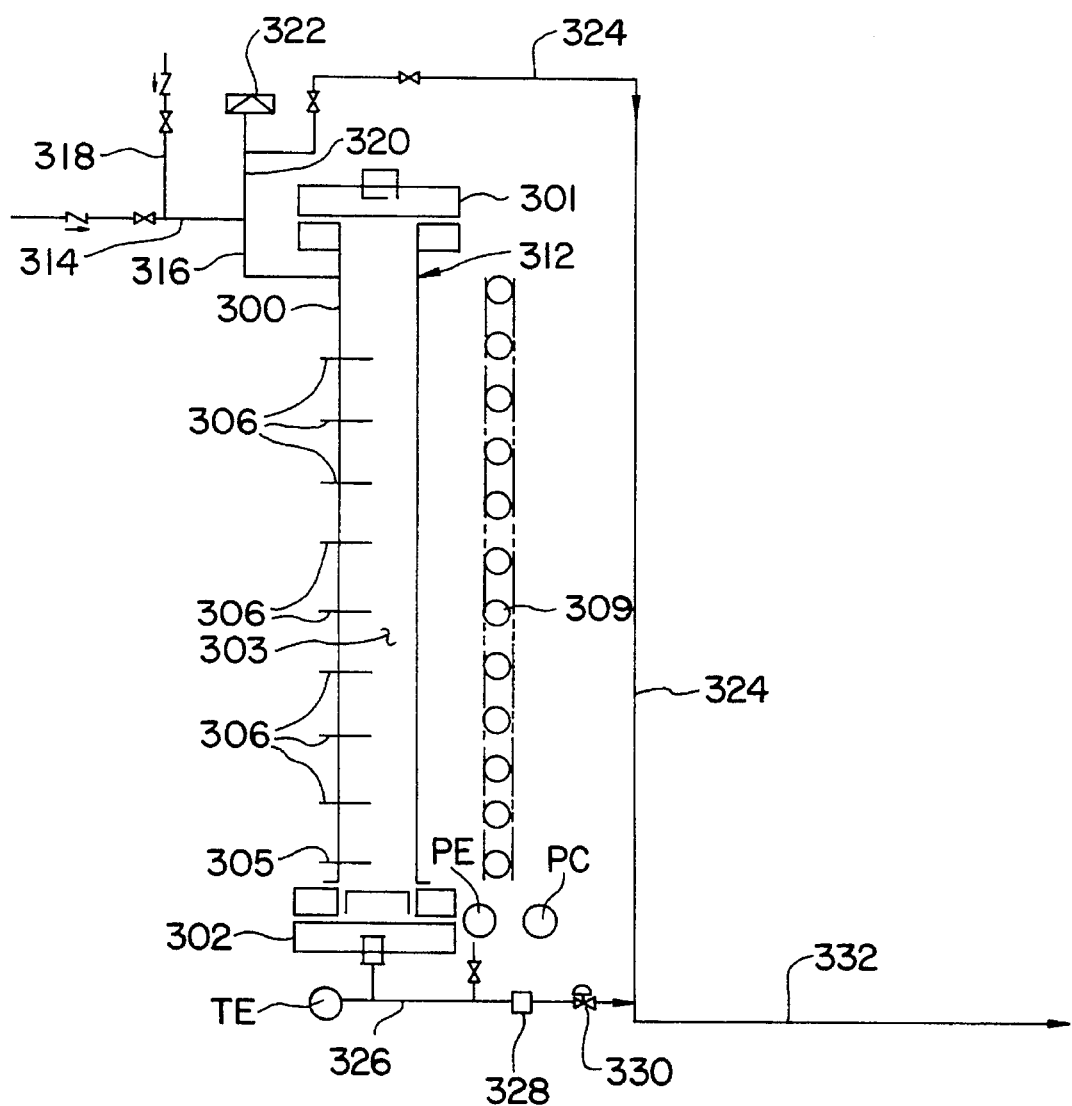
FIG. 3 is a schematic representation of an adiabatic reactor for carrying out the process of the present invention.

FIG. 3 is a schematic representation of an apparatus constructed to simulate an adiabatic reactor. The reactor 312 comprises a 2 inch diameter Schedule 10 Hastelloy pipe 300 which is 8 feet in total length. Pipe 300 of reactor 312 has a bottom end closed by a bottom flange 302 and top end closed by top flange 301. A catalyst bed 303 fills pipe 300 from a location about 6 inches above bottom flange 302 to a location approximately 42 inches from the top flange 301. Between flange 302 and the bottom of bed 303 is a spacer 304 and a few inches of activated carbon, which is non-catalytic. Temperature probe 305 is inserted in the bottom of catalyst bed 303. Eight additional internal side entering RTD (Resistance Temperature Detector) probes 306 are inserted in the bed equally spaced between temperature probe 305 and the top of bed 303. This avoids the use of a conductive thermowell. In the illustrated embodiment, the RTD probes are spaced six inches apart for a total of four feet up the side wall of reactor 312.

The reactor 312 is completely surrounded with 1 inch of preformed rigid fiberglass insulation (not shown). A copper coil 309 is wound uniformly along the axial length of reactor 312 outside of the wrapped insulation. Another 1 inch of insulation (not shown) is wrapped around the outside of coil 309. Either steam or hot oil can be fed to the coil 309 to supply external heat to minimize the driving force for heat transfer from the reactor. The insulation between the coil and the reactor is designed to minimize heat transfer in either direction.

The feed material, e.g. 142b and HF are introduced into reactor 312 via conduits 314 and 316 near the top flange 301. Nitrogen or other drying fluids can be introduced into reactor 312 via conduit 316 and 318. A suitable safety by-pass system comprising branch conduit 320, rupture disk 322 and conduit 324 is included in the system. A double pipe heat exchanger (not shown) is included in the feed system for vaporizing the R142b/HF feed mixture.

Effluent from reactor 312 is conducted via conduit 326 through in-line filter 328 and pressure control valve 330 to line 324 and line 332 to a scrubbing and drying system (not shown) for removing acids. After scrubbing and drying, the reactor effluent is sent to an on-line gas chromatography device (GC) (not shown) to analyze the product.

Example 1

The preparation and activation of the catalyst (Cr/Ni/ AlF$_3$) were performed substantially as described in Example 1A of European Patent Publication No. 0 486 333 A1, the specification of which is incorporated herein by reference.

Two hundred fifty (250) ml of a support containing, by weight, 73% aluminum fluoride and 27% alumina (obtained by hydrofluorination of HSA Alumina obtained from W. R. Grace & Co. placed in a fluidized bed reactor at 300° C. with a mixture of air and hydrofluoric acid), was placed in a rotary evaporation containing 5 to 10 volume % of hydrofluoric acid. Then, two separate aqueous solutions were prepared:

a) A chromic acid solution with nickel chloride added, containing:

Anhydrous chromic acid: 12.5 g
nickel chloride hexahydrate: 29 g
water: 40 g; and
b) A methanol solution containing:
methanol: 17.8 g
water: 50 g A mixture of these two solutions was then introduced at ambient temperature and under atmospheric pressure over about 45 minutes into the support under agitation. The catalyst was then dried under a flow of nitrogen on a fluid bed at around 100° C. for 4 hours.

For activation, the catalyst (63.1 grams) was placed into the reactor described above in relation to FIG. 3. The catalyst was dried at 300° C. using 20 cc/m of nitrogen for five hours, followed by HF gas activation (15 cc/m, which was gradually increased to 40 cc/m over 4 hours). The process of HF activation was maintained for 18 hours.

Example 2

The adiabatic reactor of FIG. 3 was packed with 5.5 lbs of Ni/Cr/Al catalyst and then activated by a procedure similar to that described in Example 1. Feed rates were 6 lbs/hr of R142b and 4 lbs/hr of HF (HF/R142b mol ratio= 3.35 ) and the pressure was 150 psig. The effluent gas was analyzed as 99,972 wt % R143a, with the balance being R142b. There were virtually no olefins down to detectable limits (i.e. <5 ppm). The axial temperature profile in the reactor measured from the top to bottom of the bed was as follows:

| Axial Length ft | Temp °C. |
| --- | --- |
| 0.0 | 121 |
| 0.5 | 123 |
| 1.0 | 125 |
| 1.5 | 127 |
| 2.0 | 130 |
| 2.5 | 134 |
| 3.0 | 148 |
| 3.5 | 284 |
| 4.0 | 271 |

The reduction in temperature between 3.5 and 4.0 ft is due to reactor heat losses. The actual maximum bed temperature is located between the two probes. To find this maximum temperature, the feed rates were lowered by 10% to shift the temperature profile up the bed. The probe at 3 ft climbed from 148° C. to a maximum of 295° C. Therefore, the adiabatic temperature rise was 174° C. (the difference between 295° C. and 121° C.).

In the above example, the ideal gas HF partial pressure was 127 psi (i.e., 0.76×165 psia). At the inlet temperature of 121° C., the HF enthalpy was about 375 Pcu/lb. This is about 74% of the enthalpy difference between the ideal gas line (432 Pcu/lb.) and the saturation curve (210 Pcu). The consequence is that about 57 Pcu/lb of HF (103 Btu/lb) in the form of heat of disassociation was available to absorb heat of reaction.

Example 3

The reactor configuration was identical to that of Example 2. Feed rates were the same as in Example 2, but pressure was lowered to 100 psig. Conversion to R143a was 99.970%, with the remainder being 142b. No olefins were detected. The axial temperature profile was:

| Axial Length ft | Temp °C. |
| --- | --- |
| 0.0 | 115 |
| 0.5 | 117 |
| 1.0 | 119 |
| 1.5 | 124 |
| 2.0 | 129 |
| 2.5 | 164 |
| 3.0 | 290 |
| 3.5 | 280 |
| 4.0 | 272 |

When the feed rates were lowered by 10% as in Example 2, the maximum bed temperature was found to be 305° C. The adiabatic temperature rise was about 17° C. higher than in Example 2. Presumably, this is because the higher superheat of the inlet gas above the dew point eliminated some of the HF disassociation endotherm.

In the above example, the ideal gas partial pressure of HF is 88 psi. At 115° C., this corresponds to an HF enthalpy of 385 Pcu/lb, which is about 82% of the difference between the ideal gas and saturation curve enthalpies (428−195=233 Pcu/lb). The amount of disassociation heat available for absorbing heat of reaction is 43 Pcu/lb (77 Btu/lb). This is about 25% less than the amount available in Example 2, which explains the higher exotherm of Example 3.

Example 4

The reactor configuration was the same as in Example 2. The feed rates were 7.0 lbs/hr of R142b and 3.5 lbs/hr of HF. This was an HF/R142b molar feed ratio of 2.5:1. The reactor pressure was 150 psig. The conversion was 99.95%, with the balance being R142b. No olefins were detected (i.e. <5 ppm). The axial temperature profile was:

| Axial Length ft | Temp °C. |
| --- | --- |
| 0.0 | 116 |
| 0.5 | 117 |
| 1.0 | 119 |
| 1.5 | 121 |
| 2.0 | 131 |
| 2.5 | 292 |
| 3.0 | 283 |
| 3.5 | 279 |
| 4.0 | 274 |

When the feed rates were lowered by 10% as in Example 2, the temperature rose to 303° C. at 2.0 ft, indicating this to be the maximum bed temperature. The adiabatic temperature rise was 187° C.

In the above example, the ideal gas HF partial pressure was 118 psi. At the initial reaction temperature of 116° C., the HF enthalpy is about 365 Pcu/lb. This represents about 70% of the difference between the ideal gas and the saturation curve (432−206=226 Pcu/lb). About 67 Pcu/lb of HF (121 Btu/lb) in heat of disassociation were available for absorbing the exotherm.

Example 5

The reactor configuration was the same as in Example 2. The feed rates were 5.0 lbs/hr R142b and 4.0 lbs/hr HF. The pressure was 150 psig. The conversion was 99.98%, with the balance being R142b. There were no olefins detected (i.e. <5 ppm). The axial temperature profile was:

| Axial Length ft | Temp °C. |
|---|---|
| 0.0 | 120 |
| 0.5 | 121 |
| 1.0 | 122 |
| 1.5 | 123 |
| 2.0 | 126 |
| 2.5 | 145 |
| 3.0 | 250 |
| 3.5 | 242 |
| 4.0 | NA |

When feed rates were lowered by 10%, the maximum bed temperature was found to be 262° C.

In the above example, the ideal gas partial pressure of HF was 132 psi. At 120° C., the HF enthalpy is about 370 Pcu/lb. This corresponds to about 71% of the difference between the ideal gas HF enthalpy and the saturation curve enthalpy (433−212=221 Pcu/lb). About 63 Pcu/lb (or 113 Btu/lb) were available in heat of disassociation to absorb heat of reaction.

Example 6

The reactor configuration and pressure (150 psig) were the same as in Example 2. The R142b flow rate was 7.5 lbs/hr and the HF flow rate was 1.8 lbs/hr, for an HF/R142b molar feed ratio of 1.8. The wt % R143a in the reactor effluent was 98.8%. There was 0.43% R142b, 690 ppm of R141b, and 230 ppm of R140a. The amounts of olefins in the reactor effluent were as follows: 5858 ppm of R1130a, 335 ppm of R1131a, and 87 ppm of R1132a. This shows that the relative rates favor production of R1130a as olefin byproduct is in an adiabatic reactor. The axial temperature profile was:

| Axial Length ft | Temp °C. |
|---|---|
| 0.0 | 108 |
| 0.5 | 110 |
| 1.0 | 114 |
| 1.5 | 119 |
| 2.0 | 154 |
| 2.5 | 336 |
| 3.0 | 324 |
| 3.5 | 316 |
| 4.0 | 306 |

When flow rates were lowered by 10%, the maximum bed temperature was found to be 356° C. This example shows that an adiabatic reactor is more effective in limiting olefin formation than a cooled (isothermal) reactor at comparable maximum temperature. In the adiabatic reactor, only a small portion of the R142b is exposed to the maximum reactor temperature. This is because the temperature is achieved by converting R142b to R143a. At the point where maximum bed temperature is achieved, very little R142b remains. By contrast, in a near isothermal system, all of the R142b is exposed to the high temperature.

Example 7

The reactor configuration was the same as in Example 2. This experiment was designed to test the feasibility of using R141b and R142b as co-feeds. The R142b feed rate was 3 lbs/hr and the R141b feed rate also was 3 lbs/hr. The HF feed rate was 3.2 lbs/hr. The molar ratio of HF in excess of its stoichiometric requirement was 1.97. Conversion of both feeds was 99.97%. R1130a was a non-selective coproduct at a level of 190 ppm. The axial temperature profile was as follows:

| Axial Length ft | Temp °C. |
|---|---|
| 0.0 | 108 |
| 0.5 | 115 |
| 1.0 | 304 |
| 1.5 | 290 |
| 2.0 | 283 |
| 2.5 | 275 |
| 3.0 | 271 |
| 3.5 | 267 |
| 4.0 | 262 |

The ideal gas HF partial pressure was about 122 psi (0.7421×165 psia). At an initial temperature of 108° C., the HF enthalpy was about 350 Pcu/lb, which accounts for about 63% of the difference between the ideal gas and saturation curve enthalpies (432−208=224 Pcu/lb).

Example 8

Example 2 is repeated except that R124 is hydrofluorinated under the same conditions. 8.15 lbs/hr of R124 and 4 lbs/hr of HF are fed for a HF/R124 mol ratio of 3.35. At a pressure of 150 psig, the reaction will be initiated in the 110° to 140° C. range. The adiabatic exotherm will be about the same as for R142b in Example 2, and the final temperature will be in the range of 270° to 315° C. Conversion to R125 will be essentially complete, with high selectivity.

While the invention has been described herein with reference to specific embodiments, it is not limited thereto. Rather it should be recognized that this invention may be practiced as outlined above within the spirit and scope of the appended claims, with such variants and modifications as may be made by those skilled in this art.

We claim:

1. A substantially adiabatic process for hydrofluorinating hydrochlorocarbons and hydrochlorofluorocarbons, which comprises contacting, in an adiabatic reactor, a starting compound having the general formula RCl, with R having the general formula $C_wH_xCl_yF_z$, wherein w is an integer from 1 to 4, inclusive, and the sum (x+y+z) is either 2w+1 or 2w−1, with gaseous HF, at a molar ratio of HF to starting compound of at least about 2.5:1, at an initial reaction pressure of from about 1 atmosphere to about 500 psig, at a reactor temperature below 400° C. and an initial HF enthalpy of from about 35% to about 90% of the difference between the enthalpy of the feed HF at its calculated ideal gas partial pressure and the enthalpy of saturated HF at the same pressure, in the presence of a catalyst that is sufficiently active to initiate the reaction in the presence of partially dissociated HF and capable of maintaining activity and selectivity at elevated temperatures.

2. The process of claim 1, wherein the initial reaction temperature is between 40° C. and 140° C.

3. The process of claim 2, wherein the initial reaction temperature is from about 90° C. to about 170° C.

4. The process of claim 1, wherein the starting compound is selected on the basis of its normal boiling point being below 60° C.

5. The process of claim 4, wherein the normal boiling point of the starting compound selected is below 50° C.

6. The process of claim 1, wherein the compound is selected on the basis of producing an exotherm greater than 2 kcal/mol as a result of the hydrofluorination reactor.

7. The process of claim 6, wherein the net exotherm is between 2 kcal/mol and 20 kcal/mol.

8. The process of claim 1, wherein the reactor is maintained at a pressure between 50 and 250 psig.

9. The process of claim 8, wherein the reactor pressure is maintained at 150 psig.

10. The process of claim 1, wherein the reactor is charged with an unsupported catalyst.

11. The process of claim 1, wherein the reactor is charged with a supported catalyst.

12. The process of claim 10, wherein said reactor is charged with a chromium salt catalyst.

13. The process of claim 10, wherein the catalyst is $CrF_3 \cdot 4H_2O$.

14. The process of claim 12, wherein there is added a cocatalyst to said chromium salt, said cocatalyst being selected from the group consisting of nickel, cobalt, zinc and manganese salts.

15. The process of claim 14, wherein said cocatalyst is nickel.

16. The process of claim 1, wherein the reactor is charged with catalyst supported on a material selected from the group consisting of activated carbon, graphite, fluorinated graphite, alumina and fluorinated alumina.

17. The process of claim 16, wherein said catalyst is supported on fluorinated alumina.

18. The process of claim 16, wherein said catalyst is $Cr/Ni/AlF_3$.

19. The process of claim 1 wherein the starting compound is one in which is selected so w is 2, y is 0 and (x+y+z) is 2w+1.

20. The process of claim 1, wherein the starting compound is R142b.

21. The process of claim 1, wherein the starting compound is a mixture of R142b and R141b.

22. The process of claim 1, wherein the starting compound is R124.

* * * * *